(12) United States Patent
Ovokaitys et al.

(10) Patent No.: US 9,999,785 B2
(45) Date of Patent: *Jun. 19, 2018

(54) METHOD AND SYSTEM FOR GENERATION AND USE OF ACTIVATED STEM CELLS

(71) Applicants: Todd Frank Ovokaitys, Carlsbad, CA (US); John Scott Strachan, Edinburgh (GB)

(72) Inventors: Todd Frank Ovokaitys, Carlsbad, CA (US); John Scott Strachan, Edinburgh (GB)

(73) Assignee: Dr. Todd Frank Ovokaitys, Carlsbad, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 14/726,457

(22) Filed: May 30, 2015

(65) Prior Publication Data
US 2015/0343234 A1    Dec. 3, 2015

Related U.S. Application Data

(60) Provisional application No. 62/006,034, filed on May 30, 2014.

(51) Int. Cl.
*A61N 5/06* (2006.01)
*A61K 35/28* (2015.01)
(Continued)

(52) U.S. Cl.
CPC .............. *A61N 5/062* (2013.01); *A61K 35/28* (2013.01); *A61K 35/51* (2013.01); *A61K 35/545* (2013.01);
(Continued)

(58) Field of Classification Search
CPC .................. A61N 5/062; A61N 5/0622; A61N 2005/0626; A61N 2005/0659;
(Continued)

(56) References Cited

U.S. PATENT DOCUMENTS 5,874,266 A    2/1999  Palsson
6,811,564 B1  11/2004  Strachan
(Continued)

FOREIGN PATENT DOCUMENTS

EP    1011697        6/2000
EP    1292134 A2 *  3/2003   ......... G02B 27/0927
(Continued)

OTHER PUBLICATIONS

Ong, Wei-Kee et al., The activation of directional stem cell motility by green light-emitting diode irradiation, Dec. 19, 2012, Biomaterials, 34: pp. 1911-1920.*

(Continued)

*Primary Examiner* — David C Eastwood
*Assistant Examiner* — Vynn Huh
(74) *Attorney, Agent, or Firm* — Novel IP

(57) ABSTRACT

Unactivated stem cells are activated by treating them with an amplitude modulated laser beam having a wavelength lying in the range of 405 to 980 nanometers. The laser beam is modulated within a range of 8 to 12 MHz. Using the activated stem cells, tissue can be repaired and regenerated by preparing the unactivated stem cells, treating the unactivated stem cells with an amplitude modulated laser beam having a pre-determined frequency for obtaining activated stem cells, administering the activated stem cells into a body containing the tissue, and using a homing beam to guide the activated stem cells within the body to the location of the tissue.

22 Claims, 5 Drawing Sheets

(51) Int. Cl.
*A61K 35/51* (2015.01)
*A61K 35/545* (2015.01)
*A61K 41/00* (2006.01)
*A61N 5/067* (2006.01)

(52) U.S. Cl.
CPC ............ *A61K 41/00* (2013.01); *A61N 5/0622* (2013.01); *A61N 2005/067* (2013.01); *A61N 2005/0626* (2013.01); *A61N 2005/0659* (2013.01); *A61N 2005/0662* (2013.01)

(58) Field of Classification Search
CPC ...... A61N 2005/0662; A61N 2005/067; A61K 35/28; A61K 35/51; A61K 35/545; A61K 41/00
USPC .......................................................... 607/88
See application file for complete search history.

(56) References Cited

U.S. PATENT DOCUMENTS

| | | | |
|---|---|---|---|
| 7,294,508 B2 | 11/2007 | Parikh | |
| 7,427,502 B2 | 9/2008 | Gostjeva | |
| 7,674,620 B2 | 3/2010 | Totey | |
| 7,829,335 B2 | 11/2010 | Inoue | |
| 8,313,477 B2 | 11/2012 | See | |
| 8,748,178 B2 | 6/2014 | Egli | |
| 8,788,213 B2 | 7/2014 | Bright | |
| 2004/0204746 A1* | 10/2004 | Ovokaitys | A61N 5/00 607/89 |
| 2005/0170506 A1 | 8/2005 | Sayre | |
| 2006/0129210 A1 | 6/2006 | Cantin | |
| 2007/0154465 A1 | 7/2007 | Kharazi | |
| 2007/0231307 A1 | 10/2007 | Tankovich | |
| 2008/0064099 A1 | 3/2008 | Parikh | |
| 2008/0176332 A1 | 7/2008 | Berns | |
| 2010/0015576 A1 | 1/2010 | Altshuler | |
| 2010/0068141 A1 | 3/2010 | Kaushal | |
| 2012/0041521 A1 | 2/2012 | Oron | |
| 2012/0101479 A1* | 4/2012 | Paspaliaris | A61K 35/12 604/522 |
| 2012/0129158 A1 | 5/2012 | Berns | |
| 2012/0215156 A1 | 8/2012 | Ishikawa | |
| 2012/0258451 A1 | 10/2012 | Klimanskaya | |
| 2014/0004601 A1 | 1/2014 | Lim | |
| 2014/0093482 A1 | 4/2014 | Paspaliaris | |
| 2014/0128800 A1* | 5/2014 | Kim | C07K 14/7158 604/20 |
| 2014/0200503 A1 | 7/2014 | Centurion | |
| 2014/0273207 A1 | 9/2014 | Chan | |
| 2014/0303546 A1 | 10/2014 | Badiavas | |
| 2014/0377831 A1 | 12/2014 | Ho | |

FOREIGN PATENT DOCUMENTS

| | | |
|---|---|---|
| EP | 1892290 | 2/2008 |
| EP | 2248888 | 11/2010 |
| JP | 2008194055 | 8/2008 |
| RU | 2291703 | 1/2007 |
| WO | 1998042356 | 10/1988 |
| WO | 1995029645 | 11/1995 |
| WO | 1996039489 | 12/1996 |
| WO | 2001068110 | 9/2001 |
| WO | 2003029402 | 1/2003 |
| WO | 2003018783 | 3/2003 |
| WO | 2004081172 | 9/2004 |
| WO | 2007014323 | 2/2007 |
| WO | 2008013985 | 3/2008 |
| WO | 2008089292 | 7/2008 |
| WO | 2009050696 | 4/2009 |
| WO | 2010005557 | 1/2010 |
| WO | 2010124585 | 11/2010 |
| WO | 2010134007 | 11/2010 |
| WO | 2011109797 | 9/2011 |
| WO | 2012071393 | 5/2012 |
| WO | 2012122081 | 9/2012 |
| WO | 2012122081 A2 | 9/2012 |
| WO | 2012131558 | 10/2012 |
| WO | 2012178156 | 12/2012 |
| WO | 2013063406 | 5/2013 |
| WO | 2014185945 | 11/2014 |
| WO | 2015053694 | 4/2015 |
| WO | 2015184421 A1 | 12/2015 |

OTHER PUBLICATIONS

International Search Report for PCT/US15/33425, dated Sep. 29, 2015.
Gatrix, "Supplementing with Light." www.cam-mag.com, CAM Nov. 2012 (2012), enitre document [online] URL=<http://perfect-tp.dyndns-ip.com/DT/perfect/images/mg_cam.pdf>.
Taylor et al., "Banking on human embryonic stem cells: estimating the number of donor cell lines needed for HLA matching", Lancet, Dec. 10, 2005; 366: pp. 2019-2025.
Office Action dated Aug. 10, 2017 for U.S. Appl. No. 15/349,886; (pp. 1-26).
International Search Report for PCT/US16/61673, dated Mar. 2, 2017.

* cited by examiner

METHOD AND SYSTEM FOR GENERATION AND USE OF ACTIVATED STEM CELLS

CROSS-REFERENCE

The present specification relies on U.S. Provisional Patent Application No. 62/006,034, entitled "Methods, Systems and Compositions for the Generation and Use of Activated Stem Cells" and filed on May 30, 2014, for priority, which is herein incorporated by reference in its entirety.

FIELD

The present specification discloses methods and systems for activating stem cells and, in particular, the use of modulated ultra-rapid laser impulses to activate and guide stem cells.

BACKGROUND

While stem cells offer therapeutic potential for the replacement of damaged or degenerated cells, therapies have been limited by an inability to effectively and efficiently guide the stem cells to a target location in sufficient numbers to achieve the desired results. In the case of an active inflammatory condition, the stem cells may be naturally attracted to the target tissue to some degree, but, in general, there is a need to increase and improve the extent to which stem cells are actively guided and/or channeled to the target location. This is especially true when attempting to treat past healed injuries, such as the spinal cord after transection.

What is needed, therefore, is a method of delivering stem cells to a treatment region, and stimulating adherence, differentiation and integration.

SUMMARY

When applying an amplitude modulated laser beam, as described below, through a flask of Kg1a cells, it has been found that the cells unexpectedly line up in a string, the cells adhering to each other where the beam had been placed. Upon examination, the primitive cells line Kg1a, which has stem cell like features, was found to have increased its expression of the hematopoietic stem cell marker CD34. Upon further review, it was also realized that the nature of the modulated laser signal would be broadly stimulating to the cell adhesion and communication molecules known as alpha and beta integrins. Flow cytometry showed a variable yet significant increase in the measurement of beta 1, beta 2 and alpha 4 integrin molecules on the cell surface that peaked in 24 hours and declined after 48 hours. Visible observations were that cell to cell and cell to surface (of the flask) adhesion were markedly increased wherever the beam was directed in a flask of cells. Accordingly, it was determined that the stimulus increases migration and localization of stem cells, while also increasing cell adhesion molecule expression in stem cells. Additionally, tissue stimulated with such a resonant signal draws stem cells to where the beam is directed and favors the cells remaining in the tissue, which has also been stimulated to be more adherent. As described further below, the beam produced through a SONG device will have much deeper depth of penetration with intact modulation. This can thus allow the directed migration and adherence of stem cells with the particular intention of increasing the yield of stem cells delivered to a target tissue in need of regeneration or repair.

The present specification is directed toward methods of repairing, regenerating, curing, or treating damaged biological tissue, such as lung tissue, kidney tissue, blood vessels, immune system cells, bone tissue, teeth, liver tissue, endocrine tissues, pituitary tissue, thymus tissue, intervertebral discs, brain tissue, spinal tissue, or nerve tissue by obtaining unactivated stem cells, forming activated stem cells from the unactivated stem cells by treating the unactivated stem cells with an amplitude modulated laser beam having a pre-defined wavelength and a pre-defined amplitude, and administering the activated stem cells into a body containing the biological tissue.

The method may further comprise using a homing beam to guide the activated stem cells within the body to the location of the biological tissue. Optionally, the pre-defined wavelength is in a range of 405 to 980 nanometers. Optionally, the laser beam is modulated in a range of 8 to 12 MHz. Optionally, prior to treating the unactivated stem cells, the laser beam is expanded in a range of two to seven times by passing the laser beam through a beam expander. Optionally, prior to treating the unactivated stem cells, the laser beam is passed through a Strachan-Ovokaitys Node Generator. Optionally, a phase cancellation of the laser beam is adjusted to achieve a predetermined power output before treating the unactivated stem cells.

Optionally, treating the unactivated stem cells comprises applying the amplitude modulated laser beam having a wavelength lying in a range of 405 to 980 nanometers to a container containing the unactivated stem cells, wherein the container is rotated at a speed of one complete rotation every 3 to 5 seconds and wherein the container is moved up and down for approximately 15 seconds simultaneous to the rotation. Optionally, the laser beam has a wavelength of 674 nm. Optionally, the unactivated stem cells are autologous or exogenous. Optionally, relative to the unactivated stem cells, the activated stem cells comprise at least one of an increased expression of an alpha or beta integrin, an increase in CD34, or an enhanced migratory action in a direction of the homing beam. Optionally, the laser beam is modulated within a range of 8 to 12 MHz. Optionally, a phase cancellation of the laser beam is adjusted to achieve a predetermined power output before treating the unactivated stem cells.

The present specification is also directed toward systems for repairing, regenerating, curing, or treating damaged biological tissue, such as lung tissue, kidney tissue, blood vessels, immune system cells, bone tissue, teeth, liver tissue, endocrine tissues, pituitary tissue, thymus tissue, intervertebral discs, brain tissue, spinal tissue, or nerve tissue. The system comprises an amplitude modulator for generating an amplitude modulated laser beam, a beam expander for expanding the amplitude modulated laser beam, a phase cancellation device for adjusting a phase cancellation of the laser beam to obtain a predetermined power output of the laser beam, a container adapted to contain stem cells, wherein the laser beam is configured to be directed toward the container for a predetermined period of time in order to form activated stem cells, and a homing beam adapted to be directed toward said damaged biological tissue and configured to guide the activated stem cells toward said damaged biological tissue.

Optionally, the system further comprises a Strachan-Ovokaitys Node Generator to obtain a predetermined wavelength of the laser beam. Optionally, the amplitude modulated laser beam has a wavelength lying in a range of 405 to 980 nanometers. Optionally, the laser beam is modulated within a range of 8 to 12 MHz. Optionally, the amplitude modulated laser beam is configured to be passed through the beam expander in order to expand the amplitude modulated laser beam in a range of 2 to 7 times. Optionally, the container is adapted to be rotated at a speed of one rotation every 3 to 5 seconds and simultaneously moved up and down for approximately 15 seconds. Optionally, after exposure to said amplitude modulated laser beam, the activated stem cells comprise at least one of an increased expression of an alpha or beta integrin, an increase in CD34, or an enhanced migratory action in a direction of the homing beam compared to the stem cells prior to exposure to said amplitude modulated laser beam.

The aforementioned and other embodiments of the present shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein.

DETAILED DESCRIPTION

Figure 1:
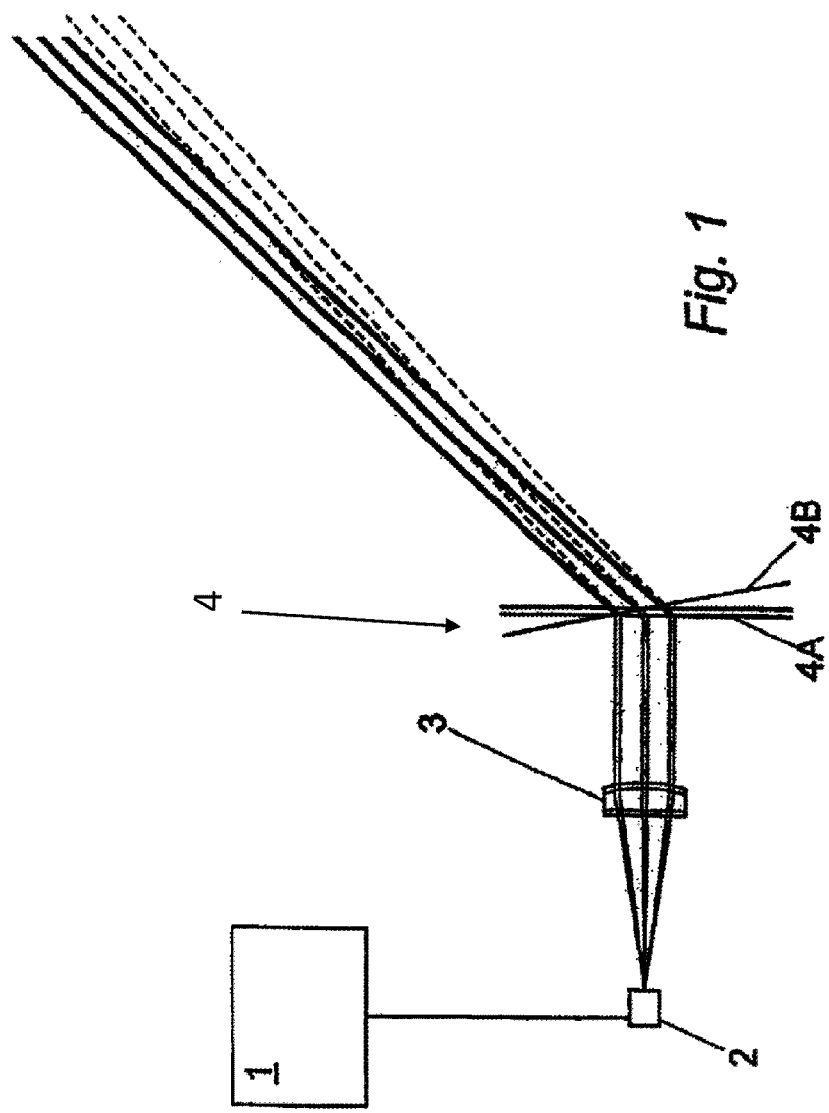
FIG. 1 illustrates a Strachan-Ovokaitys Node Generator device as disclosed in U.S. Pat. No. 6,811,564, which is incorporated herein by reference in its entirety.

The present specification is directed towards a composition of activated stem cells obtained by obtaining unactivated stem cells and applying amplitude modulated pulses of laser light to the unactivated stem cells to create said activated stem cells. In various embodiments, a stem cell may be defined as an undifferentiated cell of a multicellular organism that is capable of giving rise to substantially more cells of the same type, and from which certain other kinds of cell can arise by differentiation.

In one embodiment, the unactivated stem cells are autologous or exogenous. The pulses of laser light have a wavelength in a range of 300 to 1000 nm, and, in one embodiment, approximately 674 nm. The pulses of laser light are passed through a beam expander and are phase conjugated before being applied to the unactivated stem cells.

In various embodiments, an activated stem cell is one that, relative to the original stem cell, has at least one of the following improved traits: an increased cell surface expression of an alpha or beta integrin, more specifically alpha 4, beta 1 or beta 2 integrin, an increase in CD34, or an enhanced migratory action in the direction of the applied beam.

In another embodiment, the present specification discloses a method of treating a patient with an area of tissue in need of regeneration, reconstitution, or repair comprising administering to the patient a composition comprising the activated stem cells and, using a laser beam, guiding the activated stem cells to said area of tissue. The laser beam comprises amplitude modulated pulses of laser light. The laser beam causes a three dimensional directional localization of said activated stem cells. The adherence of activated stem cells to a target tissue is increased relative to an adherence of unactivated stem cells. In an embodiment, the method of treating results in a reversing neurologic deficits arising from cerebral palsy in said patient. In another embodiment, the method of treating results in regenerating myocardial tissue and improving cardiac function in said patient. In yet another embodiment, the method of treating results in repairing a spinal cord injury in said patient.

The various embodiments of the present specification are based on experiments applying an amplitude modulated laser beam through a flask of cells. The finding was that the cells had lined up in a string of cells adherent to each other where the beam had been placed. A primitive cell line Kg1a, which has stem cell like features, was found to have increased its expression of the hematopoietic stem cell marker CD34. Upon further review it was also realized that the nature of the modulated laser signal would be broadly stimulating to the cell adhesion and communication molecules known as alpha and beta integrins. Flow cytometry showed a variable yet significant increase in the measurement of beta 1, beta 2 and alpha 4 integrin molecules on the cell surface that peaked in 24 hours and declined after 48 hours. Visible observations were that cell to cell and cell to surface (of the flask) adhesion were markedly increased wherever the beam was directed in a flask of cells. A stimulus that will increase migration and localization of stem cells, while also increasing cell adhesion molecule expression in stem cells, as well as tissue stimulated with such a resonant signal, would tend to draw stem cells to where the beam is directed and favor their remaining in the tissue, also thus stimulated to be more adherent. As described further below, the beam produced through a SONG device will tend to have a much deeper depth of penetration with intact modulation. This can thus allow the directed migration and adherence of stem cells with the particular intention of increasing the yield of stem cells delivered to a target tissue in need of regeneration or repair.

The systems and the methods disclosed in the present specification may be used to treat every organ of the human body by using activated stem cells. By directing such stem cells towards any tissue or organ the regeneration and repair of the tissue or organ is accelerated many fold. In various embodiments, the system and methods disclosed herein may be used to rebuild lungs, kidneys, blood vessels, immune system, bones, teeth, liver, endocrine tissues such as thyroid and pancreas, pituitary and thymus, intervertebral discs, among other tissues and organs. Treatment of exemplary patient conditions, using embodiments disclosed herein, have:

Treated congestive heart failure. Patients with severe end stage disease (cardiac ejection fractions in the 15% range) have shown benefit within the day of treatment. Over 3 to 6 weeks and 2 to 3 treatments, 50-100% or greater relative increases in cardiac ejection fraction have been seen. Remarkable improvements in clinical condition and relief of symptoms have been seen and are fairly stable.

Treated Parkinson's disease. Treated patients have exhibited reduced tremors, decreased rigidity and longer walking strides with greater stability. Speech, breathing, and coordination have also been significantly improved.

Treated Multiple Sclerosis, with significant success when the cells are guided to the areas of localized neural injury. One subject who was in an acute exacerbation phase showed improved arm and leg strength, better speech, and enhanced coordination within an hour of the treatment.

Treated spinal injury. Treated patients have shown improved arm and leg function and sensation below the mid-cervical lesion evolving over 6-8 weeks after the treatment.

Treated cerebral palsy. Treated patients have shown reduced spasticity, increased range of motion, and improved fine motor coordination. A single treatment can bring new functional capacity, even for patients where standing and walking has not been present.

Treated amyotrophic lateral sclerosis (ALS, or Lou Gehrig's Disease). Protocols have shown a remarkable recovery in a rapidly progressive bulbar case (presents with speech and swallowing as opposed to these being late phase). Within one hour of the treatment, a patient had greater strength in her arms and legs, along with improved speech, swallowing and lingual coordination. Eight weeks post treatment, instead of the expected return to progression, the patient continues to be significantly improved and stable.

Treated knee injuries. Treated patients have shown rapid healing in knee cartilage tears, specifically in the menisci, and have even been able to regenerate cartilage in bone on bone situations.

Provide anti-aging treatments. Patients who have received the laser activated stem cell treatment, given for rejuvenation purposes, have shown improved function and youthfulness.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In various embodiments, for activation, the stem cells are treated with a laser process including exposing them to a predefined laser wavelength at a predefined amplitude modulation that is passed through a beam expander Strachan-Ovokaitys Node Generator or SONG device, which is disclosed in U.S. Pat. No. 6,811,564 and incorporated herein by reference.

FIG. 1 illustrates a SONG device as disclosed in U.S. Pat. No. 6,811,564. Referring to FIG. 1, the SONG device comprises a laser diode 2 which is controlled by an amplitude modulator 1. The laser diode 2 is selected to have a substantially linear relationship between current and wavelength with minimum mode hopping. The amplitude modulator 1 modulates the current to the laser diode 2 which, in turn, results in a very small wavelength modulation of the laser, for purposes discussed below.

Figure 2:
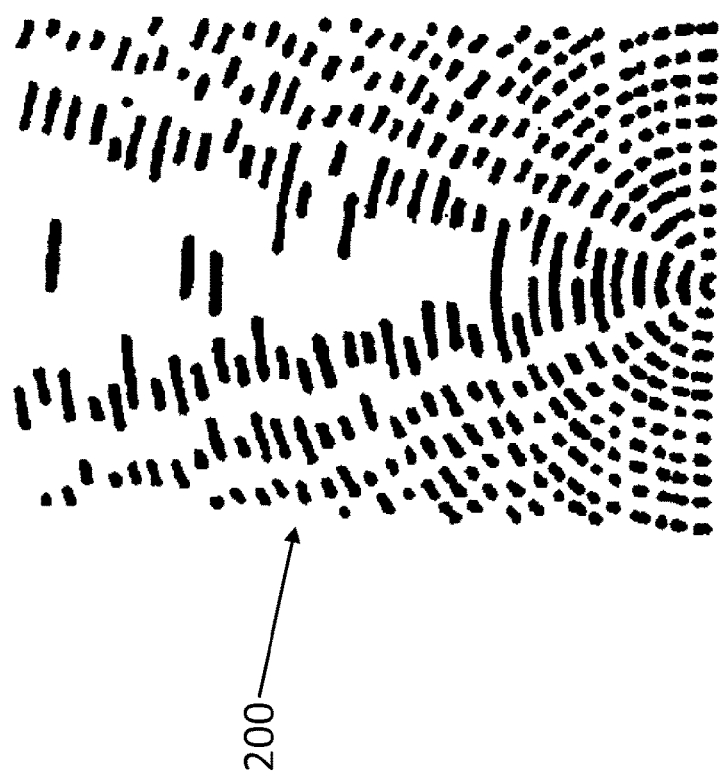
FIG. 2 shows the sparse constructive interference effect from a 1 percent bandwidth cancellation plate having a 5 mm aperture.

The output of the laser diode 2 is collimated by a lens 3 and passed to an optical element 4. The optical element 4 consists of a first diffraction grating, a refractive element, and a second diffraction grating such that the beam is substantially cancelled. This allows the cancellation to occur over a small percentage of the wavelength variance of the laser source, rather than at a single critical wavelength. Wavelengths beyond the acceptance bandwidth of the cancelling optic 4 above and below the center frequency pass without being cancelled. This means that a complex Fresnel/Fraunhoffer zone will be generated, defined by the beat frequency of the high and low frequencies as a function of the aperture. Consequently, relatively sparse zones of constructive interference will occur between the high and low frequency passes of the cancellation element in selected directions from the aperture, as shown in FIG. 2. FIG. 2 shows the sparse constructive interference effect from a 1 percent bandwidth cancellation plate of 5 mm aperture. Black represents constructive nodes.

As seen in FIG. 1, the optical element 4 can be adjusted angularly between positions 4A and 4B. This varies the ratio of constructive to destructive interference.

In effect, the continuous beam is transformed into a string of extremely short duration pulses typically of sub femto second duration. The small wavelength modulation of the laser diode 2 causes the constructive and destructive nodes to move rapidly through the volume of the Fresnel zone of the collimator lens aperture. This has the effect of stimulating very short (sub picosecond) pulse behaviour at any point in the Fresnel zone through which the nodes pass at a pulse repetition frequency defined by the modulator frequency.

The wavelength of the cancellation and constructive interference zones for a theoretical single path would be the difference between the two frequencies. If the bandwidth of the cancelling element is narrow, this difference is very small and the effective wavelength of the cancelled/non-cancelled cycle would be very long, on the order of picoseconds. Therefore, the system would behave substantially similarly to a system with no cancellation because it requires an aperture much larger than the primary light wavelength to generate a useful Fresnel/Fraunhoffer zone. Such an aperture would greatly multiply the available Feynman diagram paths eliminating any useful effect, even if it were possible to generate a sufficiently coherent source of such an aperture.

If the beat frequency can be made high enough, the wavelength of the cancelled to non-cancelled cycle can be a fraction of a practical aperture. This will make this wavelength sufficiently small to limit the Feynman paths to within a cycle or two in free space allowing the Fresnel/Fraunhoffer effect to be apparent. Since the center frequency and spectrum spread of a laser diode may be modulated by adjusting the current and or temperature of the junction, the pattern of the Fresnel/Fraunhoffer zones can be varied substantially by very small variations in the wavelength of one or both pass frequencies. Such modulation is produced in the apparatus of FIG. 1 by the modulator 2.

A conventional coherent or incoherent beam would have high probability paths in the Feynman diagram. These paths would overlap at very low frequencies (kHz) and be of little practical use in the stimulation of molecular resonance. It should be noted however that the phenomena described above may be used as a means to multiply the modulation frequency, up to the point where the beam effectively becomes continuous. Thus, by properly selecting the aperture, the region of the beam selected for transmission through the medium, and the modulation frequency, it is possible to cause the constructive nodes to pass across any given point in the beam at frequencies many times higher than the modulation frequency. In ideal conditions, the duration of exposure to a constructive node of any point would be for a period equivalent to a quarter of the duration of a wavelength of the molecular frequency repeated once per cycle.

If the wavelength of the laser is chosen to be one easily absorbed by the atomic structures it is desired to induce to resonance, then the beam will efficiently deliver the desired modulation frequency to the desired molecules. Cell adhesion molecules and human integrins such as alpha 4 and beta 1 are ideally suited for excitation to chemical activity by this method.

The sources of cells for the procedure described herein may be autologous or exogenous. Autologous refers to cells along with related tissue growth factors from the person who is to be treated with the cells. These cells will be a genetic match obviating risks of rejection of cells. In current methods, autologous stem cells are either derived or concentrated from peripheral blood, bone marrow or fat, yet other tissues could be a source of autologous stem cells as virtually every tissue of the body has its own distinct stem cell reservoir.

A preferred exogenous source of stem cells is umbilical cord blood. Stem cells from cord blood are very robust with long telomeres (a genetic aging clock level of newborn level) and a strong capacity for tissue repair. Functionally, rejection syndromes of the cells and graft versus host disease (GVHD) have not been issues with this source of cells in the context of an intact immune system. Matched bone marrow could also be a source of cells, though a high degree of matching would be required to avoid rejection and GVHD. In practice, for regeneration as opposed to anti-leukemic medical regimes, cord blood stem cells have been used safely.

Figure 3:
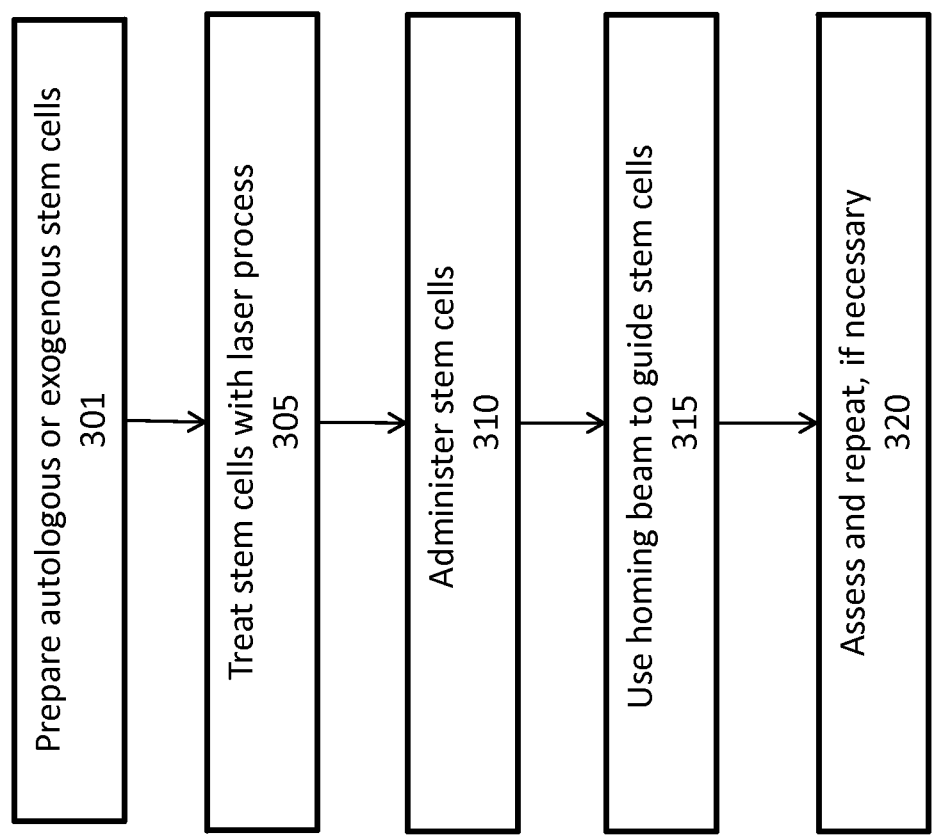
FIG. 3 is a flowchart illustrating a method of activating stem cells and using them to treat a tissue requiring treatment, in accordance with an embodiment of the present specification.

FIG. 3 is a flowchart illustrating a method of activating stem cells and using them to treat a tissue requiring treatment, in accordance with an embodiment of the present specification. Referring to FIG. 3, autologous or exogenous stem cells to be administered are pre-treated with ultra-rapid impulses of modulated laser light before administration to a patient. The general procedure comprises first preparing cells for treatment 301 by isolating autologous or exogenous stem cells in an biologically compatible solution. The stem cells are then treated with a laser process 305, including exposing them to a predefined laser wavelength at a pre-defined modulation that is passed through a beam expander Strachan-Ovokaitys Node Generator, as further described in the examples below.

The now activated stem cells are administered to a patient 310, usually by IV infusion, although other routes such as intranasal, intra-CSF, and selective intra-articular or intra-arterial injection are also possible. The stem cells are guided to the target treatment location 315 by directing a homing beam transcutaneously to the target tissue from two or more axes that intersect in the desired target volume. The patient's clinical response is assessed and the procedure is repeated 320, if necessary, until the optimal or desired results are achieved.

Figure 4:
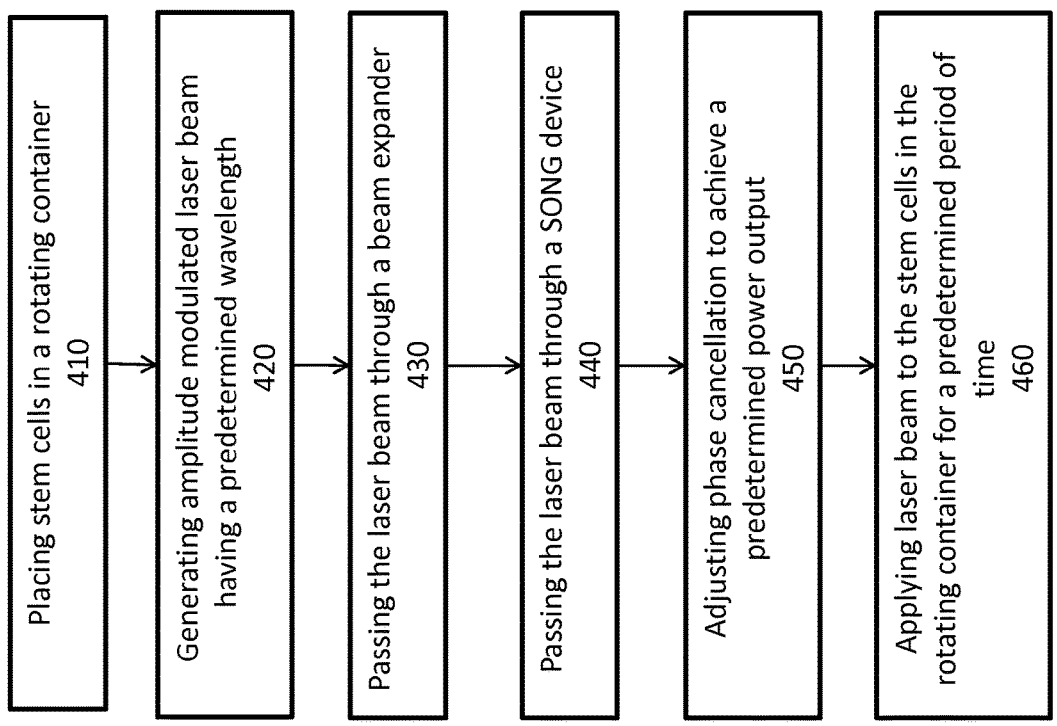
FIG. 4 illustrates the steps of activating stem cells by using a laser based process, in accordance with an embodiment of the present invention.

FIG. 4 illustrates the steps of activating stem cells by using a laser based process, in accordance with an embodiment of the present invention. In various embodiments, the steps of preparing autologous or exogenous stem cells and treating them with a laser process comprise placing the unactivated stem cells in a container which is capable of rotation 410. In an embodiment, the speed of rotation of the container is approximately one rotation per 3 to 5 seconds. In an embodiment, the container also moves in a plane perpendicular to the plane of rotation. The container moves in an upward and downward direction with respect to the plane of rotation at a speed of about 15 seconds in each direction. In an embodiment, the height of the container is a multiple of the height of a laser beam that is used to treat the unactivated stem cells.

Next at step 420, an amplitude modulated laser beam having a predetermined wavelength is generated. In various embodiments, the laser beam has a wavelength lying in the range of 405 to 980 nanometers (nm). In an embodiment, the laser beam has a wavelength of approximately 674 nm. In an embodiment, the laser beam is modulated within a range of 8 to 12 MHz.

At step 430, the laser beam is passed through a beam expander for expanding the beam approximately 2 to 7 times.

Next, at step 440 the laser beam is passed through a a Strachan-Ovokaitys Node Generator (SONG) such as one explained with reference to FIGS. 1 and 2 above.

At step 450, phase cancellation is adjusted to achieve a required power output of the laser beam. The phase cancellation is adjusted by measuring the power output, adjusting the beam to minimum cancellation as defined by the measured power being at the maximum and then changing the angle until the desired percentage calculation is reached by the measured power reducing to this level.

At step 460 the laser beam is applied to the rotating container in order to obtain activated stem cells.

In one embodiment, the above described process results in stem cells that, relative to the administration of unactivated stem cells, have an increased cell surface expression of alpha 4, beta 1 and beta 2 integrins. In one embodiment, the above described process results in stem cells that, relative to the administration of unactivated stem cells, have an approximately 30-35% increase in CD34, the hematopoietic stem cell surface marker.

Figure 5:
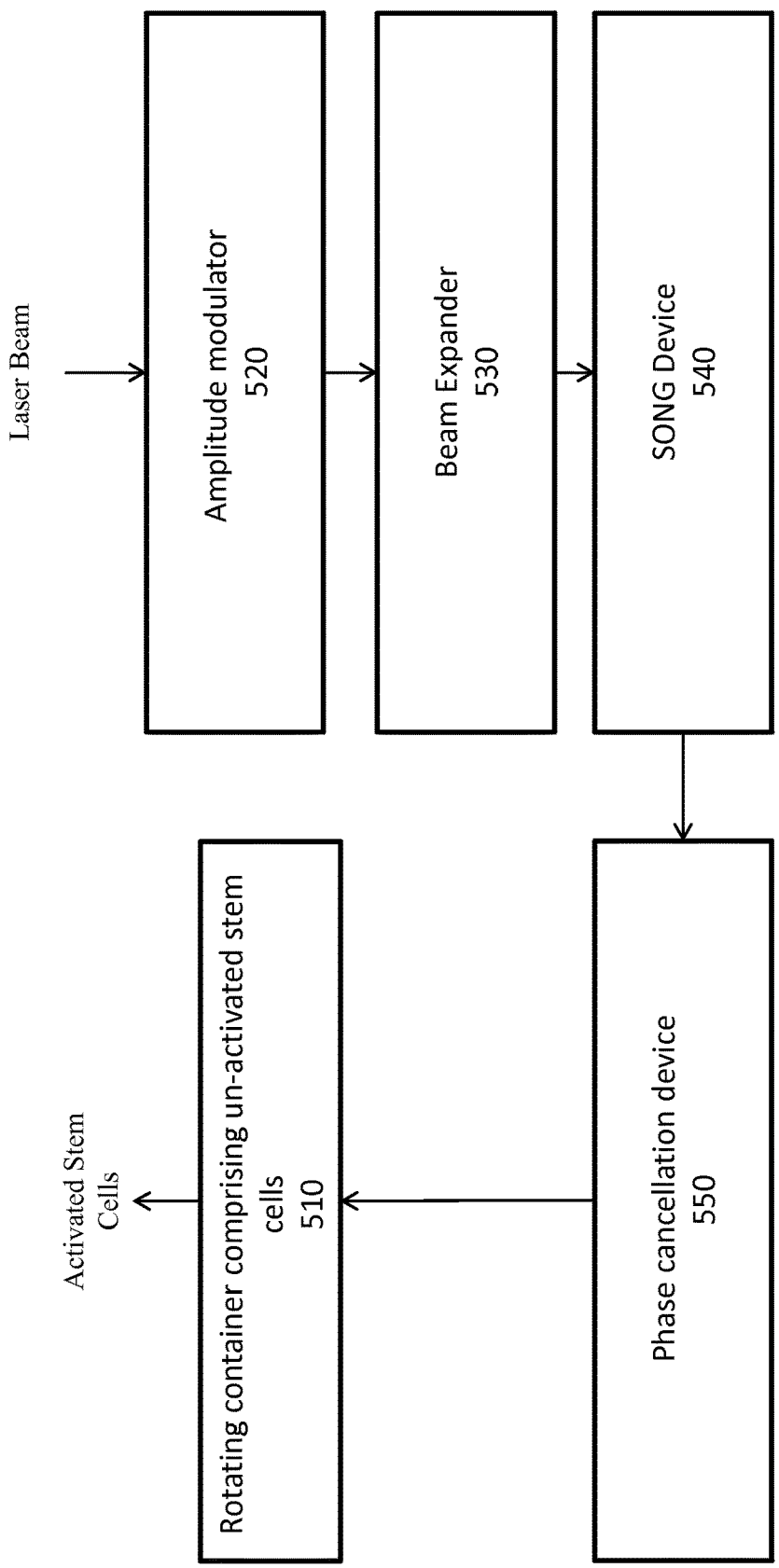
FIG. 5 is a block diagram illustrating a system for generation of activated stem cells by applying an amplitude modulated laser beam having a predetermined wavelength and power output to a container containing un-activated stem cells, in accordance with an embodiment of the present specification.

FIG. 5 is a block diagram illustrating a system for generation of activated stem cells by applying an amplitude modulated laser beam having a predetermined wavelength and power output to a container containing un-activated stem. System 500 comprises a rotating container 510 comprising un-activated stem cells, an amplitude modulator 520 for modulating a laser beam to obtain a laser beam having an amplitude modulated in the range of 405 to 980 nanometers, a beam expander 530 for expanding the laser beam two to seven times, a Strachan-Ovokaitys Node Generator 540 for obtaining a pre determined wavelength of the laser beam; and a phase cancellation device for adjusting a phase cancellation of the laser beam 550 to obtain a predetermined power output of the laser beam. In various embodiments, the container is rotated at a speed of one rotation every 3 to 5 seconds and/or is simultaneously moved up and down for approximately 15 seconds in each direction.

Example 1: Laser Guided Stem Cells to Reverse Cerebral Palsy

Patient: A 20 year old female with cerebral palsy due to hypoxic brain injury has had significant disabilities since infancy. While her cognition was fairly well preserved, she had marked spasticity and her knees had significant flexion restriction. Her speech was understandable and coherent yet breathy. Her examination was remarkable for an imbalance of conjugate gaze, with the right eye tending to drift outward. Other cranial nerve exam was fairly intact except for speech being mildly dysarthric. Her upper extremity strength was normal except for a weak grip and tone was relatively normal. In contrast, her lower extremities showed marked spasticity, with flexion to about 45 degrees at the knees, such that it was not possible to stand unassisted.

Procedure: 10 million umbilical cord blood stem cells were prepared for injection. These cells were concentrated into about 3 cc. They were treated before injection with a laser of wavelength 674 nm and modulation at 10 MHz that first passed through a 5× beam expander and then through a Strachan-Ovokaitys Node Generator, or SONG device, which as described herein.

At minimum phase cancellation through the device, the power output was 1.15 mW, which was then phase cancelled by adjusting the optics to an output of 0.46 mW. The residual light is in the form of sparse nodes of constructive interference that have much greater depth of penetration than ordinary laser light in visible wavelengths which is intensely scattered beyond 2-5 mm. The cells were activated by slowly rotating the syringe containing the cells through the beam for 77 seconds.

The activated stem cells were administered to the patient by a slow IV push over a 3 minute period of time. Upon infusion of the activated stem cells, they were directed to the brain and spinal cord with a beam slowly scanning up and down the central spine or slowly scanning back and forth, then up and down over the respective regions of the brain until the entire area had been scanned. The rate of beam movement was approximately 1-2 cm per second over the respective areas projected transcutaneously as follows:

Lower spine: 2.5 minutes
Upper Spine: 2.5 minutes
Right Occipital: 1 minute
Right Temporo-Parietal: 3 minutes
Right Frontal: 1 minute
Left Frontal: 1 minute
Left Temporo-Parietal: 3 minutes
Left Occipital: 1 minute In various embodiments, cell adhesion molecules of the stem cells get activated by application of amplitude modulated laser beam as explained above. Further activation of the stem cells takes place when these cells are guided within a body to reach a target tissue by a using the laser guidance process. In some embodiments, a photo-attraction effect from the guiding laser beam that could also be related to activation of the state of cell adhesion molecules takes place. The activity of cell adhesion molecules in the volume of tissue that the guiding laser beam stimulates makes both the stem cells and target tissue stickier. Hence, the stem cells have a greater tendency not only to stay where the guiding laser beam has been as they circulate through the body but to be instructed by the native tissue regarding the state the stem cells should attain and the manner in which they should integrate in the tissue.

In various embodiments, the area of coverage of the guiding laser beam is the area that allows directing the beam over the surface projection of the entire volume of the organ or tissue to be treated, from at least one and preferably two to three axes, the latter collimated to get the highest overall summated treatment to the desired volume of tissue. In an embodiment 20-90% phase cancellation of the guiding laser beam is carried out. In another embodiment the phase cancellation of the laser beam is within 50% to 70%. In yet another embodiment, approximately 60% phase cancellation is carried out. In various embodiments, the guiding laser beam may stay at the location of the tissue requiring treatment for the entire time of the treatment when the area requiring treatment is small as in Parkinson's disease, or may sweep a larger organ at an approximate rate of 1 to 2 cms per second.

Results: The procedure was well tolerated. Immediately afterwards she described feeling energy and tingling in her brain and body, especially in her lower legs and feet. She also felt that there was already a reduction in spastic muscle tone, and she felt calm and relaxed.

Over one week she noted a remarkable increase in lower extremity flexibility and could extend her legs to within 10-12 degrees of straight. One month later she was able to stand without assistance. Remarkably, seven weeks after the procedure she was able to walk for short distances without assistance. She also observed a significant improvement in the fine coordination of her hands and fingers, enabling her to be able to draw rectangles and triangles for the first time. Her breathing control was improved, and she noted that she could talk and be understood on a phone much better than before.

Example 2: Laser Guided Stem Cells to Regenerate Myocardial Tissue and Function

Patient: A 69 year old white male had end stage congestive cardiomyopathy with post multiple myocardial infarctions and a measured cardiac ejection fraction in the 15-17% range. His prognosis was very poor and was only given hope of sustained survival if he had an implantation of a left ventricular assist device. He was pale and cyanotic in appearance and communication was confused, consistent with a low perfusion state.

Procedure: 120 cc of peripheral blood were removed by vein from the subject. This was concentrated into 20 cc of stem cell rich plasma using a standard device for this procedure. This provided an estimated 10 million autologous blood derived stem cells.

The cells were ozonated with 15 cc of ozone, which was bubbled through the cells. The laser configuration was 674 nm modulated at 10 MHz, passed through a 5× beam expander and then phase conjugated through a SONG device from 1.80 to 0.69 mW. The stem cells were treated in the syringe with this beam for 3 minutes.

The now activated stem cells were infused into the patient by a slow IV push over a 5 minute period. Upon infusion of the activated stem cells, they were directed to the heart with a beam directed transcutaneously to the myocardium via the anterior myocardial projection from the anterior chest wall for 5 minutes and the lateral myocardial projection via the lateral chest wall for 5 minutes. The beam was directed over these respective regions in slow sweeps side to side and up and down to cover the entire myocardial region in both of these axes, with the rate about 1-2 cm per second.

Results: The procedure was well tolerated. Fifteen to twenty minutes later the patient's skin had more color and his cyanotic lips turned pink and vibrant. His confused state of mind was much clearer. By 45-60 minutes, he had increased physical energy, got out his chair and danced to music playing in the office.

This procedure was repeated twice more at approximately 3 week intervals, with the patient showing increasing recovery of strength and function. He had gone from extremely limited physical activity on the order of half a block exertional dyspnea to being able to walk several blocks and return to work. Follow-up echocardiogram after the third procedure showed a highly remarkable doubling of function to a 30-34% cardiac ejection fraction.

Example 3: Laser Guided Stem Cell Therapy to Repair Spinal Injury

Patient: A 24 year old male with quadriplegia four years after a C4-C5 fracture in a surfing accident had essentially no leg function and limited upper extremity proximal shrugging. He had a sensory level with markedly reduced sensation below the nipple line.

Procedure: Twenty million cord blood stem cells were prepared and were concentrated into about 5 cc. The laser configuration was 674 nm modulated at 10 MHz, passed through a 5× beam expander, and then phase conjugated with a SONG device from 0.85 mW to 0.33 mW. The cells were slowly rotated through the beam up and down for about 3 minutes. Five million of the cells were applied intranasally after the nasal passage had been prepped with hyaluronidase to enhance their ability to traverse the cribriform plate.

Fifteen million activated cord blood stem cells were infused into the patient by a slow IV push over a 5 minute time period. Upon infusion of the activated stem cells, they were directed to the treatment region by a laser beam which was applied transcutaneously over the C2-C8 area, sweeping vertically in slow movements over the central spine and then horizontally side to side 2.5 cm on either side of midline for a duration of 15 minutes.

Results: The procedure was well tolerated, though he had no particular subjective sensation of experience during the process itself. One week later, his sister (his primary caretaker) reported that he had more sensation in his abdominal region. He also had more physical energy and felt he could start to use light weights for his arms. Six to eight weeks later there was even more remarkable recovery, with extensive movement of his arms, including the ability to hit a tennis ball back with both palms. Some distal control was also possible with the ability to start feeding himself with some mechanical support. Using a Lokomat to mimic walking movements, he had improved to being able to support about 30% of his weight and could make kicking movements with his legs in a pool.

Example 4: Laser Guided Stem Cell Therapy to Restore Function in Multiple Sclerosis (MS)

Patient: A 52 year old white female with history of MS for 8 years presented with an exacerbation of neurologic symptoms. Primarily, she noted weakness in her left arm and left leg and problems with her speech and swallowing, which was confirmed on exam. Procedure: 30 ml of fat from her medial thigh areas was harvested and then processed to yield a concentrate of adipose tissue derived mesenchymal stem cells. Approximately 60 ml of peripheral blood was removed and processed to concentrate stem cells, much as in Example 2. These cells were both then mixed into a bag of about 150 ml of 5% dextrose half normal saline.

The laser configuration was 674 nm modulated at 10 MHz, passed through a 5× beam expander, and then phase conjugated through a SONG device from 1.40 to 0.55 mW. The stem cells were treated in the IV bag with this beam moving slowly across and side to side for 5 minutes. The combination of adipose and peripheral blood derived stem cells were then infused intravenously over 95 minutes.

Upon infusion of the activated stem cells, they were directed to the brain and spinal cord with a beam slowly scanning up and down the central spine and/or by scanning back and forth, then up and down over the respective regions of the brain until the entire area had been scanned. The rate of beam movement was approximately 1-2 cm per second over the respective areas projected transcutaneously with the laser guidance step being done both at the beginning of the infusion and again after all the cells had been infused. The first of these began 35 minutes after the start of the infusion and the second immediately at the completion of the infusion 95 minutes after it had begun. Each of these two sessions had the following pattern and respective durations:

Right Occipital: 1 minute
Right Temporo-Parietal: 3 minutes
Right Frontal: 1 minute
Left Frontal: 1 minute
Left Temporo-Parietal: 3 minutes
Left Occipital: 1 minute
Spine: 5 minutes During the first of the laser applications, the patient described significant tingling and electrical sensations throughout her face and neck and then in her upper and lower back. During the second application, she felt significant tingling through her face, neck, and speech apparatus. She felt warmth and tingling strongly when the beam was between her shoulder blades, then up and down the spine with the beam.

Results: Twenty minutes after the completion of the procedure, her strength was markedly better in her left arm, with 3/5 strength of proximal flexor and extensor muscles improved to 4.5/5 strength. The strength of her left leg proximally and distally showed an essentially full recovery from 3.5/5 to 5/5 strength. After over one year of follow up, the improvement has persisted and she has been free of exacerbations of her disease.

Example 5: Laser Guided Stem Cell Therapy to Reverse Parkinson's Disease

Patient: 71 year old white male diagnosed with Parkinson's 12 years before and had gradual progression of disease. The patient was on Mirapex, Stolevo, and Aspirin. He complained of soft speech, writing with small letters, shuffling gait, difficulty turning, and a tremor of his hands. His neurologic exam was remarkable for modest hearing loss of his right ear, motor function showing mild reduction of strength of flexing his lower legs bilaterally, finger to nose testing with a tendency to miss due to intention tremor, slow alternate finger touches, and a broad based gait with small steps that was slow with almost no arm swing, and heel to toe walking that was unstable.

Procedure: 30 ml of fat from the medial thigh areas was harvested and then processed to yield a concentrate of adipose tissue derived mesenchymal stem cells. About 60 ml of peripheral blood was removed and processed to concentrate stem cells, much as in Example 2. These cells were both then mixed into a bag of about 150 ml of 5% dextrose half normal saline.

The laser configuration was 674 nm modulated at 10 MHz, passed through a 5× beam expander, and then phase conjugated through a SONG device from 1.36 to 0.52 mW. The stem cells were treated in the IV bag with this beam moving slowly across and side to side for 5 minutes. The combination of adipose and peripheral blood derived stem cells were then infused slowly intravenously over 84 minutes.

After about 25 minutes after the infusion had begun, the laser was applied to the skin from the left lateral cranium perpendicular to the skin and targeting the substantia nigra for 3 minutes. The beam was then repositioned at about a 45 degree angle with respect to the axis of the first beam to approach the substantia nigra from 2 different axes, also for 3 minutes. This was repeated from the right side for 2 applications of 3 minutes each. Upon the infusion being completed this procedure was repeated for 2 applications of 3 minutes each on the right and left side. The procedure was well tolerated.

Results: Immediately following the completion of the protocol above, the neurologic exam was repeated and showed several improvements. Finger to nose testing was faster and more accurate with much reduced tremor. Alternate finger touching was faster and more accurate. His stride was longer and more balanced with improved arm swing. Heel to toe walking was better with more stability. Particularly striking, his speech was stronger and more resonant.

He had ups and downs after the procedure yet remained generally improved. He increased his work capacity from 2 to 3 clients daily. He had repetition of the procedure above 1 and 3 months after the initial procedure. The only difference was that the laser application was increased to applying the laser from 3 different axes focused of the substantial nigra on each side for 3 minutes each. One axis is from the lateral side of the brain parallel to the floor of the skull, the second from the top of the head, and the third roughly halfway between these. After the third procedure the patient has retained overall improvement for 10 months of follow up.

Example 6: Laser Guided Stem Cell Therapy to Improve Amyotrophic Lateral Sclerosis (ALS)

Patient: 69 year old white female diagnosed with the aggressive bulbar variant of ALS 6 months before. For 1-1.5 years she noted arm and leg weakness, right more than left, and arms with more weakness than her legs. She was unable to take off a shirt or dry her back with a towel. For 6 months she noted progressive and debilitating worsening of speech and swallowing functions. She also experienced pooling of saliva with occasional drooling, and would use saliva extractor if pooling excessive. She had to avoid buns and soft bread due to their tendency to get stuck. Over the preceding year she had lost 40 pounds. She also complained of mid to upper thoracic pain, and an MRI one year before had shown foraminal narrowing of up to moderate to severe degree of C3 through C6 spinal segments.

Her examination showed a woman who was very thin with relatively diminished body fat and muscle mass. Her neuro assessment showed slurred speech that was soft and hard to hear. She had difficulty protruding and controlling her tongue direction. Arm strength was reduced to 2-3/5 on the right and 3-4/5 on the left. Leg strength was 3/5 on the right proximally and distally and 4/5 on the left proximally and distally. Deep tendon reflexes were depressed on the right compared to the left, possibly due simply to weakness. The relaxation phase of her right ankle jerk reflex was slowed.

Procedure: The laser configuration was 674 nm modulated at 10 MHz, passed through a 5× beam expander and then phase conjugated through a SONG device from 1.28 to 0.53 mW.

There were 2 containers of cord blood stem cells (CBSCs) one of 2 ml with 50 million CBSCs and the other with 9 ml containing 100 million CBSCs. The containers were treated with the laser slowly turning them in front of the beam while moving the containers up and down for 3 minutes each.

The larger container of cells was used to inject paraspinal hotspots of inflammation at the following vertebral levels: C6, T2, T4, T12, L1, L2, L4, and L5. Injection of the right C6 area was associated with intense pain during and for several minutes after the injection. Discomfort was mild with the injection of the other paraspinal areas. Two-thirds of the 100 million cells were used for this purpose, the 33 million cells not used combined with the syringe containing 50 million cells. The 83 million cells thus derived were injected after sterile prep and anesthesia intrathecally via lumbar puncture.

The laser was scanned over the brain stem area, cervical spine and upper thoracic spine in slow sweeps dorsally from superior to inferior, then inferior to superior aspects of this zone, at about 1-2 cm per second, for a total of 8 minutes. The lumbar puncture and application of the laser were well tolerated and free of any significant adverse effects.

Results: About 10 minutes after the protocol her neurologic status was reassessed with remarkable improvements already evident. Her speech was already somewhat stronger and clearer with better control of her tongue movement and protrusion. In particular, she demonstrated and noted that her ability to articulate and differentiate the letter "m" and the letter "n" was much better. Her right arm strength had improved to be nearly equal to that of her left. The relaxation phase of her right ankle jerk reflex was less slowed.

A metabolic program to assist in clearing elevated lead and mercury levels was begun. She continued to do well with sustained improvement for 6 weeks, awaiting reduction of metals for another treatment cycle.

Example 7: Laser Guided Stem Cell Therapy to Regenerate Cartilage

Patient: A 73 year old white female injured her right knee in a kayaking accident, suffering multiple small tears of her medial meniscus. She had pain and limitation of movement for several months before the treatment. Exam of the knee showed full range of motion, mild tenderness to palpation of the medial patellar area, and mild crepitance. There was no effusion and neurovascular exam and ligaments were intact.

Procedure: 30 ml of fat from the medial thigh areas was harvested and then processed to yield a concentrate of adipose tissue derived mesenchymal stem cells. About 60 ml of peripheral blood was removed and processed to concentrate stem cells, much as in Example 2. This resulted in 3 containers of mesechymal adipose derived cells and 2 containers of peripheral blood derived stem cells of 6-8 ml each.

The laser configuration was 674 nm modulated at 10 MHz, passed through a 5× beam expander and then phase conjugated through a SONG device from 1.36 to 0.52 mW. The containers were treated with the laser slowly turning them in front of the beam while moving the containers up and down, the mesenchymal adipose derived cells for 3 minutes each and the peripheral blood derived stem cells for 2 minutes each.

After sterile prepping and draping and local anesthesia the right knee was injected with, in sequence, the following:
  7 ml adipose derived mesenchymal stem cells (MSCs)
  7 ml peripheral blood derived stem cells (PBSCs)
  7 ml MSCs
  7 ml PBSCs
  7 ml MSCs The laser was applied in slow sweeps over the right anterior knee side to side and up and down over the lower half of the knee at about 1cm per second for 5 minutes. The procedure was well tolerated with no discomfort right knee for one hour after the procedure.

This entire process was repeated twice more at one month intervals for a total of 3 sessions. All of the procedures were well tolerated and free of any significant adverse effects.

Results: 4 months following the last procedure she was usually pain free with only occasional discomfort with weight bearing. Her exam had improved with tenderness to palpation absent and crepitance reduced to minimal. Follow up MRI scan showed that most of the medial meniscus tears had fully healed with a few minimal residual defects not considered clinically significant.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of repairing damaged biological tissue comprising
obtaining unactivated stem cells;
forming activated stem cells from the unactivated stem cells by treating the unactivated stem cells with an amplitude modulated laser beam having a pre-defined wavelength and a pre-defined amplitude;
administering the activated stem cells into a body containing the damaged biological tissue; and
using a guiding laser beam to guide the activated stem cells within the body to the location of the damaged biological tissue, wherein the guiding laser beam is directed along the body using at least two different pathways that are angled with respect to each other and that intersect in the damaged biological tissue.

2. The method of claim 1 wherein the pre-defined wavelength is in a range of 405 to 980 nanometers.

3. The method of claim 1 wherein the laser beam used to treat the unactivated stem cells is modulated in a range of 8 to 12 MHz.

4. The method as claimed in claim 1 wherein, prior to treating the unactivated stem cells, the laser beam is expanded in a range of two to seven times by passing the laser beam through a beam expander.

5. The method of claim 1 wherein, prior to treating the unactivated stem cells, the laser beam is passed through a Strachan-Ovokaitys Node Generator.

6. The method as claimed in claim 1 wherein a phase cancellation of the laser beam is adjusted to achieve a predetermined power output before treating the unactivated stem cells.

7. The method as claimed in claim 1 wherein treating the unactivated stem cells comprises applying the amplitude modulated laser beam having a wavelength lying in a range of 405 to 980 nanometers to a container containing the unactivated stem cells, wherein the container is rotated and wherein the container is moved up and down for approximately 15 seconds simultaneous to the rotation.

8. The method as claimed in claim 1 wherein the laser beam used to treat the unactivated stem cells has a wavelength of 674 nm.

9. The method as claimed in claim 1 wherein the unactivated stem cells are autologous or exogenous.

10. The method as claimed in claim 1 wherein the guiding laser beam is swept over the damaged biological tissue at a rate of 1 cm to 2 cm per second thereby causing an enhanced migratory action of the activated stem cells in a direction of the guiding laser beam.

11. The method as claimed in claim 10 wherein the laser beam used to treat the unactivated stem cells has a wavelength lying in a range of 405 to 980 nanometers.

12. The method as claimed in claim 11 wherein the laser beam used to treat the unactivated stem cells is modulated within a range of 8 to 12 MHz.

13. The method of claim 1 wherein the damaged biological tissue is at least one of lung tissue, kidney tissue, blood vessels, immune system cells, bone tissue, teeth, liver tissue, endocrine tissues, pituitary tissue, thymus tissue, intervertebral discs, brain tissue, spinal tissue, or nerve tissue.

14. The method as claimed in claim 1 wherein the guiding laser beam has a 20% to 90% phase cancellation.

15. A method of repairing damaged biological tissue within a body, comprising
obtaining unactivated stem cells;
forming activated stem cells from the unactivated stem cells by treating the unactivated stem cells with an amplitude modulated laser beam having a pre-defined wavelength and a pre-defined amplitude;
administering the activated stem cells into a body containing the damaged biological tissue; and
using a guiding laser beam to guide the activated stem cells within the body to the location of the damaged biological tissue, wherein the guiding laser beam is swept over the damaged biological tissue at a rate of 1 cm to 2 cm per second thereby causing an enhanced migratory action of the activated stem cells in a direction of the guiding laser beam.

16. The method of claim 15 wherein the laser beam used to treat the unactivated stem cells is modulated in a range of 8 to 12 MHz.

17. The method as claimed in claim 15 wherein, prior to treating the unactivated stem cells, the laser beam is expanded in a range of two to seven times by passing the laser beam through a beam expander.

18. The method as claimed in claim 15 wherein, prior to treating the unactivated stem cells, the laser beam is passed through a Strachan-Ovokaitys Node Generator.

19. The method as claimed in claim 15 wherein a phase cancellation of the laser beam is adjusted to achieve a predetermined power output before treating the unactivated stem cells.

20. The method as claimed in claim 15 wherein treating the unactivated stem cells comprises applying the amplitude modulated laser beam having a wavelength lying in a range of 405 to 980 nanometers to a container containing the unactivated stem cells, wherein the container is rotated and wherein the container is moved up and down for approximately 15 seconds simultaneous to the rotation.

21. The method as claimed in claim 15 wherein the unactivated stem cells are autologous or exogenous.

22. The method of claim 15 wherein the damaged biological tissue is at least one of lung tissue, kidney tissue, blood vessels, immune system cells, bone tissue, teeth, liver tissue, endocrine tissues, pituitary tissue, thymus tissue, intervertebral discs, brain tissue, spinal tissue, or nerve tissue.

* * * * *